| United States Patent [19] | [11] 3,968,106 |
| --- | --- |
| Clauss et al. | [45] July 6, 1976 |

[54] PROCESS FOR THE MANUFACTURE OF 6-METHYL-3,4-DIHYDRO-1,2,3-OXATHIAZIN-4-ONE-2,2-DIOXIDE AND ITS USE AS SWEETENER

[75] Inventors: Karl Clauss, Rossert, Taunus; Hartmut Pietsch, Hofheim, Taunus; Erwin Schmidt, Kelkheim, Taunus; Harald Jensen, Frankfurt am Main, all of Germany

[73] Assignee: Hoechst Aktiengesellschaft, Frankfurt am Main, Germany

[22] Filed: July 16, 1975

[21] Appl. No.: 596,226

[30] Foreign Application Priority Data

July 18, 1974 Germany............................ 2434564

[52] U.S. Cl............................................. 260/243 R
[51] Int. Cl.².......................................... C07D 291/06
[58] Field of Search................................. 260/243 R

[56] References Cited
UNITED STATES PATENTS 3,917,589   11/1975   Clauss et al.......................... 260/243

*Primary Examiner*—John M. Ford
*Attorney, Agent, or Firm*—Curtis, Morris & Safford

[57] ABSTRACT

6-Methyl-3,4-dihydro-1,2,3-oxathiazin-4-one-2,2-dioxide and the nontoxic salts thereof are prepared by reacting acetone and fluorosulfonyl isocyanate in a molar proportion of from 14:1 to 150:1 at a temperature of from 0° to 60°C, distilling off the excess acetone from the reaction mixture with acetoacetamide-N-sulfofluoride and bringing about cyclization by a treatment with bases at a pH of from 5 to 12. The oxathiazinone derivatives are used as sweeteners.

7 Claims, No Drawings

PROCESS FOR THE MANUFACTURE OF 6-METHYL-3,4-DIHYDRO-1,2,3-OXATHIAZIN-4-ONE-2,2-DIOXIDE AND ITS USE AS SWEETENER

This invention relates to an improved process for the manufacture of 6-methyl-3,4-dihydro-1,2,3-oxathiazin-4-one-2,2-dioxide and to its use as sweetener.

U.S. Pat. No. 3,689,486 is concerned with 3,4-dihydro-1,2,3-oxathiazine-4-one-2,2-dioxides, the non toxic salts thereof, a process for preparing them and their use in sweetening compositions. The 2,2dioxides are prepared inter alia from ketones of the formula

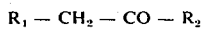

and fluorosulfonyl isocyanate (FSI). In the examples of the above specification using ketones in which $R_1$ and $R_2$ represent alkyl groups yields of about 45 to 65% of the respective oxathiazinones are obtained, while a yield of 6-methyl-3,4-dihydro-1,2,3-oxathiazin-4-one-2,2-dioxide of 13% only is obtained with acetone ($R_1 =$ H and $R_2 = CH_3$).

Other modes of preparation with better yields of the latter oxathiazinone compound have been described in the above patent specification as well as in South African Pat. Nos. 73/9560 and 74/3234, but the starting compounds used for the proposed reactions (acetoacetic acid, acetyl acetone, acetoacetic acid tert. butyl ester) are very expensive and difficultly accessible and, moreover, secondary products are partially obtained the removal of which further increases the process costs.

It is therefore the aim of the present invention to provide an improved process for the manufacture of 6-methyl-3,4-dihydro-1,2,3-oxathiazin-4-one-2,2-dioxide using acetone as starting material and giving a higher yield.

It is the object of the present invention to provide a process for the manufacture of 6-methyl-3,4-dihydro-1,2,3-oxathiazin-4-one-2,2-dioxide and the non toxic salts thereof by reacting acetone with fluorosulfonyl isocyanate (hereinafter designated "FSI") to yield acetoacetic acid amide-N-sulfofluoride and bringing about cyclization of the latter by a treatment with aqueous and/or alcoholic bases at a pH of from 5 to 12, which comprises reacting acetone and FSI in a molar proportion of from 14:1 to 150:1, preferably 25:1 to 60:1, at a temperature of from 0° to 60°C, preferably 10° to 40°C, and distilling off the excess acetone before forming the ring, preferably at a temperature below 50°C.

It is surprising that in the strongly diluted solution in dry acetone FSI gives good yields of 6-methyl-3,4-dihydro-1,2,3-oxathiazin-4-one-2,2-dioxide, whereas in concentrated solutions only minor yields can be obtained.

As shown in Examples 3 to 7, the results of which are summarized in the following Table I, the yield of the desired product strongly increases when the molar proportion of acetone to FSI is raised to a value above 10:1. It is not economical and does not offer any further advantage if a considerably higher molar proportion than 150:1 is chosen. Acetone is preferably used in a molar excess of 25 to 60:1.

The yield of the desired 6-methyl-oxathiazinone derivative decisively depends also on the temperature chosen for the reaction of acetone with FSI. At a temperature above +50°C the maximum yield is exceeded, whereas at temperatures below 0°C the long reaction period required is uneconomical. Thus reaction temperatures in the range of from +10°C to +40°C are preferred.

The process of the invention for the manufacture of 6-methyl-3,4-dihydro-1,2,3-oxathiazin-4-one-2,2-dioxide is particularly economical, since acetone is a cheap starting product which is available in large quantities.

The acetoacetamide-N-sulfofluoride, formed according to the reaction equation

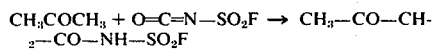

by addition of the two starting components, can be isolated as such or it can be directly reacted further without purification. To this effect, the unreacted acetone is distilled off, preferably at a temperature below 50°C to avoid secondary reactions, i.e. the distillation is suitably effected under reduced pressure. The lower limit of the distilling temperature, which, for economical reasons, is about 0°C or therebelow, essentially depends on the vacuum that can be reached.

The cyclization of the acetoacetamide-N-sulfofluoride to the oxathiazinone can be carried out in known manner, for example as described in the first mentioned specification.

Owing to the fact that the salts of the oxathiazinone obtained with organic cations, above all the alkali metal salts, and more especially the potassium salt of 6-methyl-3,4-dihydro-1,2,3-oxathiazin-4-one-2,2-dioxide, are sparingly soluble in alcohols, the cyclization to the oxathiazinone can be effected in an especially simple and advantageous manner in an alcohol, for example methanol, ethanol or isopropanol, or in mixtures thereof containing less than 50% by weight of water, preferably less than 20% by weight, with the addition of bases. The oxathiazinone salt of an inorganic base can be isolated practically quantitatively. From the salt the free oxathiazinone can be prepared in known manner without difficulty. It is particularly advantageous to add methanolic potassium hydroxide, potassium methylate, or potassium carbonate solution to a solution of the crude acetoacetamide-N-sulfofluoride in methanol. The potassium salt of 6-methyl-3,4-dihydro-1,2,3-oxathiazin-4-one-2,2-dioxide separates in the form of crystals and can be filtered off with suction whereas the potassium fluoride formed essentially remains in solution so that it can be readily separated from the oxathiazine derivative. The ring formation on methanolic solution is, therefore, a preferred embodiment of the process of the invention, since the oxathiazinone obtained is substantially free from fluoride, which is of extreme importance when the compound is used as sweetener.

For further purification, if any, the crude potassium salt of the oxathiazinone can be recrystallized from boiling water, optionally with addition of charcoal and filtering aids and obtained in a pure state. An addition of calcium hydroxide promotes the separation of traces of fluoride as insoluble $CaF_2$, which can be readily separated from the solution.

A control of purity of the 6-methyl-3,4-dihydro-1,2,3-oxathiazin-4-one-2,2-dioxide and of its salts is possible by simple UV measurement in dilute solution as the product shows a high absorption maximum at 225– 228 nm with $\epsilon =$ about $1 \times 10^4$.

The following examples illustrate the invention.

EXAMPLE 1

1.50 l (about 21 moles) of freshly distilled acetone which had been dried over $P_2O_5$ were cooled to 0°C and at said temperature 40.0 ml (0.5 mole) of FSI (molar proportion acetone:FSI 42:1) were added dropwise over a period of 20 minutes. The mixture was kept at 0°–+5°C for a further hour and then for 4 hours at room temprature until all FSI had reacted (IR control). The excess acetone was distilled off rapidly under reduced pressure and the crystalline residue (acetoacetamide-N-sulfofluoride) was dissolved in 200 ml water. After addition of 1.0 mole aqueous sodium hydroxide solution, acidification with 100 ml concentrated hydrochloric acid and extraction with ethyl acetate 75 G of crude 6-methyl-3,4-dihydro-1,2,3-oxathiazin-4-one-2,2-dioxide were obtained. For purification the crude acid was transformed into its potassium salt which was precipitated from methanolic solution with methanolic potassium hydroxide solution. For further purification the potassium salt was recrystallized from boiling water. 66 g of pure potassium salt (65% of theory) were obtained, calculated on FSI used.

EXAMPLE 2

While stirring at 20°C, 40 ml (0.5 mole) FSI were added dropwise to 2.0 l (about 28 moles) dried and freshly distilled acetone (molar proportion 1:56) and the mixture was kept for 4.5 hours at 24°C. The excess acetone was distilled off under reduced pressure at a maximum final temperature of +35°C. An oil was obtained which crystallized under cooling. The crystalline magma was made into a paste with little chloroform and the purified crystals were filtered off with strong suction. They melted at 81°–83°C. The yield amounted to 65 g of acetoacetamide-N-sulfofluoride (0.36 mole).

To bring about cyclization the acetoacetamide-N-sulfofluoride was dissolved at 10°–20°C in 200 ml methanol and at said temperature 120 ml 6.1 N methanolic potassium hydroxide solution, prepared from KOH of 86% strength and methanol were added dropwise. Stirring of the mixture was continued for 30 minutes at 30°–40°C, the mixture was cooled to 20°C and filtered with suction. The residue was carefully washed twice with methanol, the crystals were filtered off with suction and dried under reduced pressure. 64 g of the potassium salt of 6-methyl-3,4-dihydro-1,2,3-oxathiazin-4-one-2,2-dioxide were obtained, corresponding to 64% of the theory, calculated on the amount of FSI used.

EXAMPLES 3–7

These examples are intended to illustrate the dependence of the oxathiazinone yield on the FSI concentration in the starting reaction mixture with acetone at a reaction temperature of 10°C. In the following Table I are indicated the molar proportions of the starting components acetone and FSI, the amount of acetone used in ml, the FSI concentration in the acetone in mole/l, the yield of crude potassium salt of oxathiazinone in g, the content of the potassium salt in the crude product in % by weight, determined by UV analysis, and the yield of oxathiazinone, calculated from the preceding value and referred to the amount of FSI used. In the table the expression oxathiazinone designates the 6-methyl-3,4-dihydro-1,2,3-oxathiazin-4-one-2,2-dioxide.

To carry out the reaction 20 ml (0.25 mole) of FSI were dropped at 0°C to the amount indicated in Table I of dried and freshly distilled acetone and the reaction mixture was allowed to react for some hours at +10°C until the isocyanate band could no longer be observed at 4.4 μ. The excess acetone was then removed quickly by distillation in vacuo (thin layer evaporator), the residue taken up in water, 0.5 mole aqueous sodium hydroxide solution was added and the reaction mixture was exhaustively extracted with ethyl acetate. The crude product isolated from the ethyl acetate was dissolved in methanol and the potassium salt was precipitated by adding dropwise 50 ml of 5N methanolic potassium hydroxide solution. After washing and drying of the crude potassium salt of oxathiazinone at 100°C under reduced pressure the content of 6-methyl-3,4-dihydro-1,2,3-oxathiazin-4-one-2,2-dioxide was determined by comparative extinction measurement at $\lambda = 227$ nm.

EXAMPLES 8–11

These examples are intended to illustrate the influence of the temperature on the reaction of FSI with acetone with a molar proportion of acetone: FSI of 28:1 and on the oxathiazinone yield. In each reaction 500 ml (about 6.9 moles) of acetone were used and the concentration of FSI in the acetone was 0.5 mole/l in each reaction. In Table II are indicated the reaction temperature (°C), the duration of the reaction in minutes, the yield of crude oxathiazinone acid in g, the yield of crude potassium salt of oxathiazinone in g and the content of the potassium salt in % by weight, determined by UV analysis, and the yield of oxathiazone, calculated from the latter value and referred to the amount of FSI used. In thise case, too, the expression oxathiazinone designates 6-methyl-3,4-dihydro-1,2,3-oxathiazin-4-one-2,2-dioxide.

At the temperature indicted in Table II, 20.0 ml (0.25mole) FSI were added dropwise, while stirring during the course of one hour, to 500 ml (about 6.9 moles) of dried and freshly distilled acetone. The reaction mixture was then stirred at the indicated until the isocyanate band at 4.4 μ had disappeared in the IR spectrum (duration of reaction). The excess acetone was then quickly distilled off in a thin layer evaporator under reduced pessure, and the residue was taken up in water. By adding 0.5 mole sodium hydroxide solution the oxathiazinone ring was formed. The crude oxathiazinone acid was obtained by acidification with concentrated hydrochloric acid and extraction with ethyl acetate. The crude acid was isolated and, after neutralization with methanolic potassium hydroxide solution, the crystalline potassium salt of 6-methyl-3,4-dihydro-1,2,3-oxathiazin-4-one-2,2-dioxide was obtained. For complete purification the crude potassium salt obtained was recrystallized from boiling water with the addition of 1–2% by weight of calcium hydroxide, calculated on the crude potassium salt, to separate traces of fluoride.

TABLE I

| Example | molar proportion acetone: FSI | acetone used (ml) | FSI concentration in acetone (abt. mole/l) | yield of crude K salt of oxa-thiazinone g | content of K-oxathiazinone in crude product (% by weight) (UV analysis) | yield of oxa-thiazinone calculated on FSI (% of theory) |
| --- | --- | --- | --- | --- | --- | --- |
| 3[-)] | 7 : 1 | 125 | 2.0 | 30.5 | about 35 | 21 |
| 4 | 14 : 1 | 250 | 1.0 | 34.5 | about 50 | 34 |
| 5 | 28 : 1 | 500 | 0.5 | 37.0 | 76 ± 2 | 56 |
| 6 | 42 : 1 | 750 | 0.33 | 36.2 | 90 ± 1 | 64 |
| 7 | 56 : 1 | 1000 | 0.25 | 35.8 | 92 ± 1 | 65 |

[-)]comparative example

TABLE II

| Example | reaction temperature (°C) | duration of reaction (minutes) | yield of crude oxa-thiazinone (g) | yield of crude K salt of oxathia-zinone (g) | content of K-salt in crude product (% by weight) (UV analysis) | yield of oxa-thiazinone, calculated on FSI (% of theory) |
| --- | --- | --- | --- | --- | --- | --- |
| 8 | 10 | 500 | 40.2 | 37.0 | 76 ± 2 | 56 |
| 9 | 25 | 200 | 38.9 | 35.4 | 77 ± 2 | 54 |
| 10 | 35 | 80 | 36.8 | 34.6 | 84 ± 2 | 58 |
| 11 | 50 | 63 | 30.5 | 23.5 | 87 ± 2 | 41 |

What is claimed is:

1. In the process for the manufacture of 6-methyl-3,4-dihydro-1,2,3-oxathiazin-4-one-2,2-dioxide or the nontoxic salts thereof by reacting acetone and fluorosulfonyl isocyanate to obtain acetoaceticamide-N-sulfofluoride and bringing about cyclization thereof by a treatment with an aqueous or alcoholic base or a combination thereof at a pH of from 5 to 12, the improvement which comprises reacting acetone and fluorosulfonyl isocyanate at a temperature of from 0° to 60°C in a molar proportion of from 14:1 to 150:1 and distilling off the excess acetone before cyclization.

2. The process of claim 1, wherein the molar proportion of acetone to fluorosulfonyl isocyanate is in the range of from 25:1 to 60:1.

3. The process of claim 1, wherein the acetone and fluorosulfonyl isocyanate are reacted at a temperature of from 10° to 40°C.

4. The process of claim 1, wherein the excess acetone is distilled off at a temperature below 50°C.

5. The process of claim 1, wherein the oxathiazinone ring is formed in alcoholic solution containing less than 50% by weight of water by the action of bases.

6. The process of claim 5, wherein the alcoholic solution contains less than 20% by weight of water.

7. The process of claim 5, wherein methanol is used as alcohol and potassium methylate, potassium hydroxide, potassium carbonate, or a mixture thereof is used as base.

* * * * *